US008367380B2

(12) United States Patent
Blattner et al.

(10) Patent No.: US 8,367,380 B2
(45) Date of Patent: Feb. 5, 2013

(54) COMPOSITIONS AND METHODS FOR AMINO ACID BIOSYNTHESIS

(75) Inventors: Frederick R. Blattner, Madison, WI (US); Sun Chang Kim, Daejeon (KR); Jun Hyoung Lee, Daejeon (KR)

(73) Assignee: Scarab Genomics LLC, Madison, WI (US)

( * ) Notice: Subject to any disclaimer, the term of this patent is extended or adjusted under 35 U.S.C. 154(b) by 228 days.

(21) Appl. No.: 12/863,958

(22) PCT Filed: Feb. 19, 2009

(86) PCT No.: PCT/US2009/034534
§ 371 (c)(1),
(2), (4) Date: Jul. 21, 2010

(87) PCT Pub. No.: WO2009/105551
PCT Pub. Date: Aug. 27, 2009

(65) Prior Publication Data
US 2010/0330623 A1    Dec. 30, 2010

Related U.S. Application Data

(60) Provisional application No. 61/030,835, filed on Feb. 22, 2008.

(51) Int. Cl.
*C12P 13/24* (2006.01)

(52) U.S. Cl. .................................................. 435/107
(58) Field of Classification Search ................. 435/107
See application file for complete search history.

(56) References Cited

PUBLICATIONS

Sequence alignment between Accession No. ADV85741 and Applicants SEQ Id No. 1 (2005).*
Battesti, A., et al., "Acyl Carrier Protein/SpoT Interaction, the Switch Linking SpoT-Dependent Stress Response to Fatty Acid Metabolism," Molecular Microbiology, vol. 62, No. 4, pp. 1048-1063 (2006).
Gropp, Michal, et al., "Regulation of *Escherichia coli* ReIA Requires Oligomerization of the C-Terminal Domain," Journal of Bacteriology, vol. 183, No. 2, pp. 570-579 (2001).
International Search Report of PCT/US2009/034534 dated May 25, 2009.
Martinez-Costa Oscar H., et al., "The ReIA/SpoT-Homologous Gene in Streptomyces Coelicolor Encodes Both Ribosome-Dependent (p)ppGpp-Synthesizing and-degrading Activities," Journal of Bacteriology, vol. 180, No. 16, pp. 4123-4132 (1998).

* cited by examiner

*Primary Examiner* — Tekchand Saidha
(74) *Attorney, Agent, or Firm* — Morgan, Lewis & Bockius LLP (57) ABSTRACT

The present invention relates generally to compositions and methods useful for, inter alia, production of commercial biologic products such as amino acids. More specifically, the present invention relates to genetically modified strains of microorganisms and the use thereof for the production of commercial products. The present invention also provides, inter alia, novel isolated DNA, nucleic acid, vectors and reduced genome bacteria.

8 Claims, 2 Drawing Sheets

COMPOSITIONS AND METHODS FOR AMINO ACID BIOSYNTHESIS

CROSS-REFERENCE TO RELATED APPLICATIONS

The present application is a national stage of International Patent Application No. PCT/US2009/034534, filed Feb. 19, 2009, which claims the benefit of U.S. Provisional Application No. 61/030,835, filed Feb. 22, 2008, the contents of which are incorporated herein by reference.

FIELD OF THE INVENTION

The present invention relates generally to compositions and methods useful for, inter alia, production of commercial biologic products such as amino acids. More specifically, the present invention relates to genetically modified strains of microorganisms and the use thereof for the production of commercial products. The present invention also provides, inter alia, novel isolated DNA, nucleic acid, vectors and reduced genome bacteria.

SUMMARY OF THE INVENTION

In one embodiment, the present invention provides an isolated DNA, the nucleotide sequence of which comprises or consists of any one of SEQ ID NO: 1, SEQ ID NO: 2, SEQ ID NO: 3 or SEQ ID NO: 4 or a complement thereof.

In another embodiment, the present invention provides an isolated nucleic acid comprising or consisting of any one of SEQ ID NO: 1, SEQ ID NO: 2, SEQ ID NO: 3 or SEQ ID NO: 4 or a complement thereof.

In another embodiment, the present invention provides an isolated nucleic acid comprising or consisting of the nucleotide sequence of SEQ ID NO: 1, SEQ ID NO: 2, SEQ ID NO: 3 or SEQ ID NO: 4 (or a complement thereof) or of a degenerate variant thereof.

In another embodiment, the present invention provides an expression vector, for example a plasmid, comprising the nucleic acid of SEQ ID NO: 1, SEQ ID NO: 2, SEQ ID NO: 3 or SEQ ID NO: 4 operably linked to an expression control sequence. In another embodiment, the present invention provides a cultured cell comprising one of the foregoing vectors. In still another embodiment, the present invention provides a cultured cell transfected with the one of the foregoing vectors, or a progeny of said cell.

In yet another embodiment, the present invention provides a reduced genome bacterium, for example E. coli, having a genome containing a relA gene wherein the relA gene contains at least one point mutation. In a related embodiment, the mutation is at position 547 or 548 of the relA gene.

In still another embodiment, the present invention provides a bacterium having a genome that is genetically engineered to be at least 5%, at least 8% or at least 10% smaller than the genome of its native parent strain, wherein the bacterium comprises at least one relA mutation. In one embodiment, the at least one relA mutation occurs at position 547 or 548 of the relA gene. In another embodiment, the mutation is selected from one or more of: a G➔ A point mutation at position 547 of the relA gene, a G➔ T point mutation at position 547 of the relA gene, a C➔ G point mutation at position 548 of the relA gene, or a C➔ T point mutation at position 548 of the relA gene. In another embodiment, the bacterium comprises a small plurality, for example 1 to about 10, 1 to about 8 or 1 to about 5 relA point mutations occurring between positions 540 and 550 of the relA gene.

In another embodiment, the present invention provides a method of biosynthesizing an amino acid using one or more reduced genome bacterium as described herein, the method comprising: (1) providing a bacterium having DNA comprising a native relA gene; (2) replacing the native relA gene with a mutant relA gene to form a relA mutant bacterium; and (3) expressing an amino acid from the mutant relA bacterium. In one embodiment, the amino acid is selected from Ala, Arg, Asn, Asp, Cys, Glu, Gly, His, Ile, Val, Leu, Lys, Met, Phe, Pro, Ser, Thr, Tyr, and Trp.

DETAILED DESCRIPTION OF THE INVENTION

While the present invention is capable of being embodied in various forms, the description below of several embodiments is made with the understanding that the present disclosure is to be considered as an exemplification of the invention, and is not intended to limit the invention to the specific embodiments illustrated. Headings are provided for convenience only and are not to be construed to limit the invention in any way. Embodiments illustrated under any heading may be combined with embodiments illustrated under any other heading.

It is to be understood that any ranges, ratios and ranges of ratios that can be formed by any of the numbers or data present herein represent further embodiments of the present invention. This includes ranges that can be formed that do or do not include a finite upper and/or lower boundary. Accordingly, the skilled person will appreciate that many such ratios, ranges, and ranges of ratios can be unambiguously derived from the data and numbers presented herein and all represent embodiments of the present invention.

Before the present compounds, products and compositions and methods are disclosed and described, it is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

TABLES 1-4 below set forth mutant relA DNA sequences.

TABLE 1

E. coli relA coding sequence comprising a
G ➔ A mutation at position 547 (SEQ ID NO: 1).
The mutated amino acid is
underlined and shown in bold.

ATGGTTGCGGTAAGAAGTGCACATATCAATAAGGCTGGTGAATTTGATCC

GGAAAAATGGATCGCAAGTCTGGGTATTACCAGCCAGAAGTCGTGTGAGT

GCTTAGCCGAAACCTGGGCGTATTGTCTGCAACAGACGCAGGGGCATCCG

GATGCCAGTCTGTTATTGTGGCGTGGTGTTGAGATGGTGGAGATCCTCTC

GACATTAAGTATGGACATTGACACGCTGCGGGCGGCGCTGCTTTTCCCTC

TABLE 1-continued

E. coli relA coding sequence comprising a
G → A mutation at position 547 (SEQ ID NO: 1).
The mutated amino acid is
underlined and shown in bold.

TGGCGGATGCCAACGTAGTCAGCGAAGATGTGCTGCGTGAGAGCGTCGGT

AAGTCGGTCGTTAACCTTATTCACGGCGTGCGTGATATGGCGGCGATCCG

CCAGCTGAAAGCGACGCACACTGATTCTGTTTCCTCCGAACAGGTCGATA

ACGTTCGCCGGATGTTATTGGCGATGGTCGATGATTTTCGCTGCGTAGTC

ATCAAACTGGCGGAGCGTATTGCTCATCTGCGCGAAGTAAAAGATGCGCC

GGAAGATGAACGTGTACTGGCGGCAAAAGAGTGTACCAACATCTACACAC

CGCTGGCTAACCGTCTCGGAATCGGACAACTGAAATGGGAACTGGAAGAT

TACTGCTTCCGTTACCTCCATCCAACCGAATACAAACGAATTGCCAAACT

GCTGCATGAACGGCGTCTCGACCGCGAACACTACATCGAAGAGTTCGTTG

GTCATCTGCGCGCTGAGATGAAAGCTGAAGGCGTTAAAGCGGAAGTGTAT

GGTCGTCCGAAACACATCTACAGCATCTGGCGTAAAATGCAGAAAAAGAA

CCTCGCCTTTGATGAGCTGTTTGATGTGCGTGCGGTACGTATTGTCGCCG

AGCGTTTACAGGATTGCTATGCCGCACTGGGGATAGTGCACACTCACTAT

CGCCACCTGCCGGATGAGTTTGACGATTACGTCGCTAACCCGAAACCAAA

CGGTTATCAGTCTATTCATACCGTGGTTCTGGGGCCGGGTGGAAAAACCG

TTGAGATCCAAATCCGCACCAAACAGATGCATGAAGATGCAGAGTTGGGT

GTTGCTGCGCACTGGAAATATAAAGAGGGCGCGGCTGCTGGCGGCGCACG

TTCGGGACATGAAGACCGGATTGCCTGGCTGCGTAAACTGATTGCGTGGC

AGGAAGAGATGGCTGATTCCGGCGAAATGCTCGACGAAGTACGTAGTCAG

GTCTTTGACGACCGGGTGTACGTCTTTACGCCGAAAGGTGATGTCGTTGA

TTTGCCTGCGGGATCAACGCCGCTGGACTTCGCTTACCACATCCACAGTG

ATGTCGGACACCGCTGCATCGGGGCAAAAATTGGCGGGCGCATTGTGCCG

TTCACCTACCAGCTGCAGATGGGCGACCAGATTGAAATTATCACCCAGAA

ACAGCCGAACCCCAGCCGTGACTGGTTAAACCCAAACCTCGGTTACGTCA

CAACCAGCCGTGGGCGTTCGAAAATTCACGCCTGGTTCCGTAAACAGGAC

CGTGACAAAAACATTCTGGCTGGGCGGCAAATCCTTGACGACGAGCTGGA

ACATCTGGGGATCAGCCTGAAAGAAGCAGAAAAACATCTGCTGCCGCGTT

ACAACTTCAATGATGTCGACGAGTTGCTGGCGGCGATTGGTGGCGGGGAT

ATCCGTCTCAATCAGATGGTGAACTTCCTGCAATCGCAATTTAATAAGCC

GAGTGCCGAAGAGCAGGACGCCGCCGCGCTGAAGCAACTTCAGCAAAAAA

GCTACACGCCGCAAAACCGCAGTAAAGATAACGGTCGCGTGGTAGTCGAA

GGTGTTGGCAACCTGATGCACCACATCGCGCGCTGCTGCCAGCCGATTCC

TGGAGATGAGATTGTCGGCTTCATTACCCAGGGGCGCGGTATTTCAGTAC

ACCGCGCCGATTGCGAACAACTGGCGGAACTGCGCTCCCATGCGCCAGAA

CGCATTGTTGACGCGGTATGGGGTGAGAGCTACTCCGCCGGATATTCGCT

GGTGGTCCGCGTGGTAGCTAATGATCGTAGTGGGTTGTTACGTGATATCA

CGACCATTCTCGCCAACGAGAAGGTGAACGTGCTTGGCGTTGCCAGCCGT

TABLE 1-continued

E. coli relA coding sequence comprising a
G → A mutation at position 547 (SEQ ID NO: 1).
The mutated amino acid is
underlined and shown in bold.

AGCGACACCAAACAGCAACTGGCGACCATCGACATGACCATTGAGATTTA

CAACCTGCAAGTGCTGGGGCGCGTGCTGGGTAAACTCAACCAGGTGCCGG

ATGTTATCGACGCGCGTCGGTTGCACGGGAGTTAG

TABLE 2

E. coli relA coding sequence comprising a
G → T mutation at position 547 (SEQ ID
NO: 2). The mutated amino acid is
underlined and shown in bold.

ATGGTTGCGGTAAGAAGTGCACATATCAATAAGGCTGGTGAATTTGATCC

GGAAAAATGGATCGCAAGTCTGGGTATTACCAGCCAGAAGTCGTGTGAGT

GCTTAGCCGAAACCTGGGCGTATTGTCTGCAACAGACGCAGGGGCATCCG

GATGCCAGTCTGTTATTGTGGCGTGGTGTTGAGATGGTGGAGATCCTCTC

GACATTAAGTATGGACATTGACACGCTGCGGGCGGCGCTGCTTTTCCCTC

TGGCGGATGCCAACGTAGTCAGCGAAGATGTGCTGCGTGAGAGCGTCGGT

AAGTCGGTCGTTAACCTTATTCACGGCGTGCGTGATATGGCGGCGATCCG

CCAGCTGAAAGCGACGCACACTGATTCTGTTTCCTCCGAACAGGTCGATA

ACGTTCGCCGGATGTTATTGGCGATGGTCGATGATTTTCGCTGCGTAGTC

ATCAAACTGGCGGAGCGTATTGCTCATCTGCGCGAAGTAAAAGATGCGCC

GGAAGATGAACGTGTACTGGCGGCAAAAGAGTGTACCAACATCTACTCAC

CGCTGGCTAACCGTCTCGGAATCGGACAACTGAAATGGGAACTGGAAGAT

TACTGCTTCCGTTACCTCCATCCAACCGAATACAAACGAATTGCCAAACT

GCTGCATGAACGGCGTCTCGACCGCGAACACTACATCGAAGAGTTCGTTG

GTCATCTGCGCGCTGAGATGAAAGCTGAAGGCGTTAAAGCGGAAGTGTAT

GGTCGTCCGAAACACATCTACAGCATCTGGCGTAAAATGCAGAAAAAGAA

CCTCGCCTTTGATGAGCTGTTTGATGTGCGTGCGGTACGTATTGTCGCCG

AGCGTTTACAGGATTGCTATGCCGCACTGGGGATAGTGCACACTCACTAT

CGCCACCTGCCGGATGAGTTTGACGATTACGTCGCTAACCCGAAACCAAA

CGGTTATCAGTCTATTCATACCGTGGTTCTGGGGCCGGGTGGAAAAACCG

TTGAGATCCAAATCCGCACCAAACAGATGCATGAAGATGCAGAGTTGGGT

GTTGCTGCGCACTGGAAATATAAAGAGGGCGCGGCTGCTGGCGGCGCACG

TTCGGGACATGAAGACCGGATTGCCTGGCTGCGTAAACTGATTGCGTGGC

AGGAAGAGATGGCTGATTCCGGCGAAATGCTCGACGAAGTACGTAGTCAG

GTCTTTGACGACCGGGTGTACGTCTTTACGCCGAAAGGTGATGTCGTTGA

TTTGCCTGCGGGATCAACGCCGCTGGACTTCGCTTACCACATCCACAGTG

ATGTCGGACACCGCTGCATCGGGGCAAAAATTGGCGGGCGCATTGTGCCG

TTCACCTACCAGCTGCAGATGGGCGACCAGATTGAAATTATCACCCAGAA

ACAGCCGAACCCCAGCCGTGACTGGTTAAACCCAAACCTCGGTTACGTCA

CAACCAGCCGTGGGCGTTCGAAAATTCACGCCTGGTTCCGTAAACAGGAC

TABLE 2-continued

E. coli relA coding sequence comprising a
G → T mutation at position 547 (SEQ ID
NO: 2). The mutated amino acid is
underlined and shown in bold.

CGTGACAAAACATTCTGGCTGGGCGGCAAATCCTTGACGACGAGCTGGA

ACATCTGGGGATCAGCCTGAAAGAAGCAGAAAAACATCTGCTGCCGCGTT

ACAACTTCAATGATGTCGACGAGTTGCTGGCGGCGATTGGTGGCGGGGAT

ATCCGTCTCAATCAGATGGTGAACTTCCTGCAATCGCAATTTAATAAGCC

GAGTGCCGAAGAGCAGGACGCCGCCGCGCTGAAGCAACTTCAGCAAAAA

GCTACACGCCGCAAAACCGCAGTAAAGATAACGGTCGCGTGGTAGTCGAA

GGTGTTGGCAACCTGATGCACCACATCGCGCGCTGCTGCCAGCCGATTCC

TGGAGATGAGATTGTCGGCTTCATTACCCAGGGGCGCGGTATTTCAGTAC

ACCGCGCCGATTGCGAACAACTGGCGGAACTGCGCTCCCATGCGCCAGAA

CGCATTGTTGACGCGGTATGGGGTGAGAGCTACTCCGCCGGATATTCGCT

GGTGGTCCGCGTGGTAGCTAATGATCGTAGTGGGTTGTTACGTGATATCA

CGACCATTCTCGCCAACGAGAAGGTGAACGTGCTTGGCGTTGCCAGCCGT

AGCGACACCAAACAGCAACTGGCGACCATCGACATGACCATTGAGATTTA

CAACCTGCAAGTGCTGGGGCGCGTGCTGGGTAAACTCAACCAGGTGCCGG

ATGTTATCGACGCGCGTCGGTTGCACGGGAGTTAG

TABLE 3

E. coli relA coding sequence comprising a
C → G mutation at position 548 (SEQ ID
NO: 3). The mutated amino acid is
underlined and shown in bold.

ATGGTTGCGGTAAGAAGTGCACATATCAATAAGGCTGGTGAATTTGATCC

GGAAAAATGGATCGCAAGTCTGGGTATTACCAGCCAGAAGTCGTGTGAGT

GCTTAGCCGAAACCTGGGCGTATTGTCTGCAACAGACGCAGGGGCATCCG

GATGCCAGTCTGTTATTGTGGCGTGGTGTTGAGATGGTGGAGATCCTCTC

GACATTAAGTATGGACATTGACACGCTGCGGGCGGCGCTGCTTTTCCCTC

TGGCGGATGCCAACGTAGTCAGCGAAGATGTGCTGCGTGAGAGCGTCGGT

AAGTCGGTCGTTAACCTTATTCACGGCGTGCGTGATATGGCGGCGATCCG

CCAGCTGAAAGCGACGCACACTGATTCTGTTTCCTCCGAACAGGTCGATA

ACGTTCGCCGGATGTTATTGGCGATGGTCGATGATTTTCGCTGCGTAGTC

ATCAAACTGGCGGAGCGTATTGCTCATCTGCGCGAAGTAAAAGATGCGCC

GGAAGATGAACGTGTACTGGCGGCAAAAGAGTGTACCAACATCTACGGAC

CGCTGGCTAACCGTCTCGGAATCGGACAACTGAAATGGGAACTGGAAGAT

TACTGCTTCCGTTACCTCCATCCAACCGAATACAAACGAATTGCCAAACT

GCTGCATGAACGGCGTCTCGACCGCGAACACTACATCGAAGAGTTCGTTG

GTCATCTGCGCGCTGAGATGAAAGCTGAAGGCGTTAAAGCGGAAGTGTAT

GGTCGTCCGAAACACATCTACAGCATCTGGCGTAAAATGCAGAAAAAGAA

CCTCGCCTTTGATGAGCTGTTTGATGTGCGTGCGGTACGTATTGTCGCCG

TABLE 3-continued

E. coli relA coding sequence comprising a
C → G mutation at position 548 (SEQ ID
NO: 3). The mutated amino acid is
underlined and shown in bold.

AGCGTTTACAGGATTGCTATGCCGCACTGGGGATAGTGCACACTCACTAT

CGCCACCTGCCGGATGAGTTTGACGATTACGTCGCTAACCCGAAACCAAA

CGGTTATCAGTCTATTCATACCGTGGTTCTGGGGCCGGGTGGAAAAACCG

TTGAGATCCAAATCCGCACCAAACAGATGCATGAAGATGCAGAGTTGGGT

GTTGCTGCGCACTGGAAATATAAAGAGGGCGCGGCTGCTGGCGGCGCACG

TTCGGGACATGAAGACCGGATTGCCTGGCTGCGTAAACTGATTGCGTGGC

AGGAAGAGATGGCTGATTCCGGCGAAATGCTCGACGAAGTACGTAGTCAG

GTCTTTGACGACCGGGTGTACGTCTTTACGCCGAAAGGTGATGTCGTTGA

TTTGCCTGCGGGATCAACGCCGCTGGACTTCGCTTACCACATCCACAGTG

ATGTCGGACACCGCTGCATCGGGGCAAAAATTGGCGGGCGCATTGTGCCG

TTCACCTACCAGCTGCAGATGGGCGACCAGATTGAAATTATCACCCAGAA

ACAGCCGAACCCCAGCCGTGACTGGTTAAACCCAAACCTCGGTTACGTCA

CAACCAGCCGTGGGCGTTCGAAAATTCACGCCTGGTTCCGTAAACAGGAC

CGTGACAAAACATTCTGGCTGGGCGGCAAATCCTTGACGACGAGCTGGA

ACATCTGGGGATCAGCCTGAAAGAAGCAGAAAAACATCTGCTGCCGCGTT

ACAACTTCAATGATGTCGACGAGTTGCTGGCGGCGATTGGTGGCGGGGAT

ATCCGTCTCAATCAGATGGTGAACTTCCTGCAATCGCAATTTAATAAGCC

GAGTGCCGAAGAGCAGGACGCCGCCGCGCTGAAGCAACTTCAGCAAAAA

GCTACACGCCGCAAAACCGCAGTAAAGATAACGGTCGCGTGGTAGTCGAA

GGTGTTGGCAACCTGATGCACCACATCGCGCGCTGCTGCCAGCCGATTCC

TGGAGATGAGATTGTCGGCTTCATTACCCAGGGGCGCGGTATTTCAGTAC

ACCGCGCCGATTGCGAACAACTGGCGGAACTGCGCTCCCATGCGCCAGAA

CGCATTGTTGACGCGGTATGGGGTGAGAGCTACTCCGCCGGATATTCGCT

GGTGGTCCGCGTGGTAGCTAATGATCGTAGTGGGTTGTTACGTGATATCA

CGACCATTCTCGCCAACGAGAAGGTGAACGTGCTTGGCGTTGCCAGCCGT

AGCGACACCAAACAGCAACTGGCGACCATCGACATGACCATTGAGATTTA

CAACCTGCAAGTGCTGGGGCGCGTGCTGGGTAAACTCAACCAGGTGCCGG

ATGTTATCGACGCGCGTCGGTTGCACGGGAGTTAG

TABLE 4

E. coli relA coding sequence comprising a
C → T mutation at position 548 (SEQ ID
NO: 4). The mutated amino acid is
underlined and shown in bold.

ATGGTTGCGGTAAGAAGTGCACATATCAATAAGGCTGGTGAATTTGATCC

GGAAAAATGGATCGCAAGTCTGGGTATTACCAGCCAGAAGTCGTGTGAGT

GCTTAGCCGAAACCTGGGCGTATTGTCTGCAACAGACGCAGGGGCATCCG

GATGCCAGTCTGTTATTGTGGCGTGGTGTTGAGATGGTGGAGATCCTCTC

GACATTAAGTATGGACATTGACACGCTGCGGGCGGCGCTGCTTTTCCCTC

TABLE 4-continued

E. coli relA coding sequence comprising a
C → T mutation at position 548 (SEQ ID
NO: 4). The mutated amino acid is
underlined and shown in bold.

TGGCGGATGCCAACGTAGTCAGCGAAGATGTGCTGCGTGAGAGCGTCGGT

AAGTCGGTCGTTAACCTTATTCACGGCGTGCGTGATATGGCGGCGATCCG

CCAGCTGAAAGCGACGCACACTGATTCTGTTTCCTCCGAACAGGTCGATA

ACGTTCGCCGGATGTTATTGGCGATGGTCGATGATTTTCGCTGCGTAGTC

ATCAAACTGGCGGAGCGTATTGCTCATCTGCGCGAAGTAAAAGATGCGCC

GGAAGATGAACGTGTACTGGCGGCAAAAGAGTGTACCAACATCTACGTAC

CGCTGGCTAACCGTCTCGGAATCGGACAACTGAAATGGGAACTGGAAGAT

TACTGCTTCCGTTACCTCCATCCAACCGAATACAAACGAATTGCCAAACT

GCTGCATGAACGGCGTCTCGACCGCGAACACTACATCGAAGAGTTCGTTG

GTCATCTGCGCGCTGAGATGAAAGCTGAAGGCGTTAAAGCGGAAGTGTAT

GGTCGTCCGAAACACATCTACAGCATCTGGCGTAAAATGCAGAAAAAGAA

CCTCGCCTTTGATGAGCTGTTTGATGTGCGTGCGGTACGTATTGTCGCCG

AGCGTTTACAGGATTGCTATGCCGCACTGGGGATAGTGCACACTCACTAT

CGCCACCTGCCGGATGAGTTTGACGATTACGTCGCTAACCCGAAACCAAA

CGGTTATCAGTCTATTCATACCGTGGTTCTGGGGCCGGGTGGAAAAACCG

TTGAGATCCAAATCCGCACCAAACAGATGCATGAAGATGCAGAGTTGGGT

GTTGCTGCGCACTGGAAATATAAAGAGGGCGCGGCTGCTGGCGGCGCACG

TTCGGGACATGAAGACCGGATTGCCTGGCTGCGTAAACTGATTGCGTGGC

AGGAAGAGATGGCTGATTCCGGCGAAATGCTCGACGAAGTACGTAGTCAG

GTCTTTGACGACCGGGTGTACGTCTTTACGCCGAAAGGTGATGTCGTTGA

TTTGCCTGCGGGATCAACGCCGCTGGACTTCGCTTACCACATCCACAGTG

ATGTCGGACACCGCTGCATCGGGGCAAAAATTGGCGGGCGCATTGTGCCG

TTCACCTACCAGCTGCAGATGGGCGACCAGATTGAAATTATCACCCAGAA

ACAGCCGAACCCCAGCCGTGACTGGTTAAACCCAAACCTCGGTTACGTCA

CAACCAGCCGTGGGCGTTCGAAAATTCACGCCTGGTTCCGTAAACAGGAC

CGTGACAAAACATTCTGGCTGGGCGGCAAATCCTTGACGACGAGCTGGA

ACATCTGGGGATCAGCCTGAAAGAAGCAGAAAAACATCTGCTGCCGCGTT

ACAACTTCAATGATGTCGACGAGTTGCTGGCGGCGATTGGTGGCGGGGAT

ATCCGTCTCAATCAGATGGTGAACTTCCTGCAATCGCAATTTAATAAGCC

GAGTGCCGAAGAGCAGGACGCCGCCGCGCTGAAGCAACTTCAGCAAAAAA

GCTACACGCCGCAAAACCGCAGTAAAGATAACGGTCGCGTGGTAGTCGAA

GGTGTTGGCAACCTGATGCACCACATCGCGCGCTGCTGCCAGCCGATTCC

TGGAGATGAGATTGTCGGCTTCATTACCCAGGGGCGCGGTATTTCAGTAC

ACCGCGCCGATTGCGAACAACTGGCGGAACTGCGCTCCCATGCGCCAGAA

CGCATTGTTGACGCGGTATGGGGTGAGAGCTACTCCGCCGGATATTCGCT

GGTGGTCCGCGTGGTAGCTAATGATCGTAGTGGGTTGTTACGTGATATCA

CGACCATTCTCGCCAACGAGAAGGTGAACGTGCTTGGCGTTGCCAGCCGT

AGCGACACCAAACAGCAACTGGCGACCATCGACATGACCATTGAGATTTA

CAACCTGCAAGTGCTGGGGCGCGTGCTGGGTAAACTCAACCAGGTGCCGG

ATGTTATCGACGCGCGTCGGTTGCACGGGAGTTAG

In one embodiment, the present invention provides an isolated DNA, the nucleotide sequence of which comprises or consists of any one of SEQ ID NO: 1, SEQ ID NO: 2. SEQ ID NO: 3 or SEQ ID NO: 4 or a complement thereof.

In another embodiment, the present invention provides an isolated nucleic acid comprising or consisting of anyone of SEQ ID NO: 1, SEQ ID NO: 2, SEQ ID NO: 3 or SEQ ID NO: 4 or a complement thereof.

In another embodiment, the present invention provides an isolated nucleic acid comprising or consisting of the nucleotide sequence of SEQ ID NO: 1, SEQ ID NO: 2, SEQ ID NO: 3 or SEQ ID NO: 4 (or a complement thereof) or of a degenerate variant thereof.

In another embodiment, the present invention provides an expression vector, for example a plasmid, comprising the nucleic acid of SEQ ID NO: 1, SEQ ID NO: 2, SEQ ID NO: 3 or SEQ ID NO: 4 operably linked to an expression control sequence. In another embodiment, the present invention provides a cultured cell comprising one of the foregoing vectors. In still another embodiment, the present invention provides a cultured cell transfected with the one of the foregoing vectors, or a progeny of said cell.

In yet another embodiment, the present invention provides a reduced genome bacterium, for example E. coli, having a genome containing a relA gene wherein the relA gene contains at least one point mutation. In a related embodiment, the mutation is at position 547 or 548 of the relA gene.

In still another embodiment, the present invention provides a bacterium having a genome that is genetically engineered to be at least 5%, at least 8% or at least 10% smaller than the genome of its native parent strain, wherein the bacterium comprises at least one relA mutation. In one embodiment, the at least one relA mutation occurs at position 547 or 548 of the relA gene. In another embodiment, the mutation is selected from one or more of: a G→A point mutation at position 547 of the relA gene, a G→T point mutation at position 547 of the relA gene, a C→G point mutation at position 548 of the relA gene, or a C→T point mutation at position 548 of the relA gene. In another embodiment, the bacterium comprises a small plurality, for example 1 to about 10, 1 to about 8 or 1 to about 5 relA point mutations occurring between positions 540 and 550 of the relA gene.

In another embodiment, the present invention provides a method of biosynthesizing an amino acid using one or more reduced genome bacterium as described herein, the method comprising: (1) providing a bacterium having DNA comprising a native relA gene; (2) replacing the native relA gene with a mutant relA gene to form a relA mutant bacterium; and (3) expressing an amino acid from the mutant relA bacterium. In one embodiment, the amino acid is selected from Ala, Arg, Asn, Asp, Cys, Gln, Glu, Gly, His, Ile, Val, Leu, Lys, Met, Phe, Pro, Ser, Thr, Tyr, and Trp.

Definitions.

"Base pair" used herein may refer to the hydrogen bonded nucleotides of, for example, adenine (A) with thymine (T), or of cytosine (C) with guanine (G) in a double-stranded DNA molecule. In RNA, uracil (U) is substituted for thymine. Base pair may also be used as a unit of measure for DNA length.

"Clone" used in reference to an insert sequence and a vector may mean ligation of the insert sequence into the vector or its introduction by recombination either homologous, site specific or illegitimate as the case may be. When used in reference to an insert sequence, a vector, and a host cell, the term may mean to make copies of a given insert sequence. The term may also refer to a host cell carrying a cloned insert sequence, or to the cloned insert sequence itself.

"Complement," "complementary" or "complementarity" used herein may mean Watson-Crick or Hoogsteen base pairing between nucleotides or nucleotide analogs of nucleic acid molecules. For example, the sequence 5'-A-G-T-3' is complementary to the sequence 3'-T-C-A-5'. Complementarity may be "partial," in which only some of the nucleotides are matched according to the base pairing rules. Or, there may be "complete" or "total" complementarity between the nucleic acids. The degree of complementarity between nucleic acid strands may have effects on the efficiency and strength of hybridization between nucleic acid strands.

"Encoding" or "coding" used herein when referring to a nucleic acid may mean a sequence of nucleotides, which upon transcription into RNA and subsequent translation into protein, would lead to the synthesis of a given protein, peptide or amino acid sequence. Such transcription and translation may actually occur in vitro or in vivo, or may be strictly theoretical based on the standard genetic code.

"Enzyme" used herein may mean a protein which acts as a catalyst to induce a chemical change in other compounds, thereby producing one or more products from one or more substrates. Enzymes are referred to herein using standard nomenclature or by their EC number, as recommended by the Nomenclature Committee of the International Union of Biochemistry and Molecular Biology as of Mar. 11, 2004.

"Expression control sequence" used herein may mean a promoter or array of transcription factor binding sites that direct transcription of a nucleic acid operatively linked thereto.

"Free end" used in reference to a double-stranded nucleic acid may mean a linear nucleic acid with blunt free ends or sticky free ends, or a combination thereof.

"Gene" used herein may refer to a nucleic acid (e.g., DNA or RNA) that comprises a nucleic acid sequence encoding a polypeptide or precursor thereto. The polypeptide can be encoded by a full length coding sequence or by any portion of the coding sequence so long as the desired activity or functional properties (e.g., enzymatic activity, ligand binding, signal transduction, antigenicity etc.) of the full-length or fragment are retained. The term also encompasses the sequences located adjacent to the coding region on both the 5' and 3' ends that contribute to the gene being transcribed into a full-length mRNA. The term "gene" encompasses both cDNA and genomic forms of a gene. A genomic form or clone of a gene may contain the coding region interrupted with non-coding sequences termed (e.g., introns).

"Introduce" or "introduced" when used in reference to adding a nucleic acid to a strain, may mean that the nucleic acid may be integrated into the chromosome of the strain or contained on a vector, such as a plasmid, in the strain.

"Library" used herein may refer to a plurality of vectors each comprising an insert sequence or to a plurality of nucleotide fragments.

"Mutant" or "mutagenesis" used herein may mean any modification to the nucleic acid of a parent strain. Mutagenesis of nucleic acid may be of any type including, but not limited to, deletion, insertion, substitution, rearrangement, and suppressor and point mutations.

"Nucleic acid" used herein may mean any nucleic acid containing molecule including, but not limited to, DNA or RNA. The term encompasses sequences that include any base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5 carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracils, 5-methoxyaminomethyl-2-thiouracil, y-D-maninosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methyl ester, uracil-5-oxyacetic acid, pseudouracil, queosine, 2-thiocytosine, and 2,6-diaminopurine.

"Nucleotide" used herein may refer to a monomeric unit of nucleic acid (e.g. DNA or RNA) consisting of a pentose sugar moiety, a phosphate group, and a nitrogenous heterocyclic base. The base may be linked to the sugar moiety via the glycosidic carbon (1' carbon of the pentose). The combination of base and sugar may be called a nucleoside. When the nucleoside contains a phosphate group bonded to the 3' or 5' position of the pentose, it may be referred to as a nucleotide. A sequence of operatively linked nucleotides may be referred to as a "base sequence" or "nucleotide sequence" or "nucleic acid sequence," and may be represented herein by a formula whose left to right orientation is in the conventional direction of 5'-terminus to 3'-terminus.

"Operably linked" used herein may refer to an expression control sequence and downstream polynucleotide, such that productive transcription of the polynucleotide is initiated at the expression control sequence.

"Overexpressing" used herein may mean that the total cellular activity of protein encoded by a gene is increased. The total cellular activity of a protein may be due to increased cellular amounts of a protein, or increased half-life of the protein. Total cellular amounts of a protein may be increased by methods including, but not limited to, amplification of the gene coding said protein or operatively linking a strong promoter to the gene coding said protein.

"Protein" used herein may mean a peptide, polypeptide and protein, whether native or recombinant, as well as fragments, derivatives, homologs, variants and fusions thereof.

"Region of comparison" used herein when referring to a genome may be $1\times10^7$, $1.5\times10^7$, $2\times10^7$, $2.5\times10^7$, $3\times10^7$, $3.5\times10^6$, $4\times10^7$ or more nucleotides or base pairs, and when referring to a nucleic acid sequence may be 50, 100, 250, 500, $10^3$, $5\times10^3$, $10^4$, $5\times10^4$, $10^5$, $5\times10^5$, $10^6$ or more nucleotides or more base pairs.

"Stringent hybridization conditions" used herein may mean conditions under which a first nucleic acid sequence will specifically or selectively hybridize to a second nucleic acid sequence, such as in a complex mixture of nucleic acids, but to no other sequences. Stringent conditions are sequence-dependent and will be different in different circumstances. Generally, stringent conditions are selected to be about 5-10° C. lower than the thermal melting point (Tm) for the specific sequence at a defined ionic strength pH. The Tm may be the temperature (under defined ionic strength, pH, and nucleic concentration) at which 50% of the first sequence hybridizes to the second sequence at equilibrium (as the second sequences are present in excess, at Tm, 50% of the first sequence are occupied at equilibrium). Stringent conditions may be those in which the salt concentration is less than about 1.0 M sodium ion, typically about 0.01-1.0 M sodium ion concentration (or other salts) at pH 7.0 to 8.3 and the temperature is at least about 30° C. for short nucleic acid sequences (e.g., about 10-50 nucleotides) and at least about 60° C. for long nucleic acid sequences (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC and 0.1% SDS at 65° C.

"Substantially complementary" used herein may mean that a first sequence is at least 60%, 65%, 70%, 75%, 80%, 85%, 90%, 95%, 97%, 98% or 99% identical to the complement of a second sequence over a region of comparison or that the two sequences hybridize under stringent hybridization conditions.

"Substantially identical" used herein may mean that a first and second sequence are at least 60%, 65%, 70%, 75%, 80%, 85%, 90%, 95%, 97%, 98% or 99% identical or substantially complementary over a region of comparison. A reference sequence and a test sequence may be aligned, manually or by a computer algorithm (e.g., GAP, BESTFIT, FASTA and TFAST), and the percentage identity calculated by dividing "the total number of identical residues" by "the total number of residues in the reference sequence" and then multiplying by 100.

Reduced Genome Strains

Bacteria in their natural environment are exposed to many conditions that are not normally experienced in standard industrial or laboratory growth, and thus carry a large number of condition-dependent, stress-induced genes or otherwise nonessential genes which may not be needed in industrial or laboratory use of the organisms. It was realized that much of the genetic information contained within the genome of a bacteria strain could be deleted without detrimental effect to use of bacteria cultures in processes of industrial or laboratory importance. It was also recognized that a bacterium with a reduced genome might be advantageous over native strains in many industrial and laboratory applications. For example, a bacterium with a reduced genome is at least somewhat less metabolically demanding and thus can produce a desired product more efficiently. In addition, a reduced genome can lead to fewer native products and lower levels of certain native proteins, allowing easier purification of a desired protein from the remaining bacterial proteins. Furthermore, some bacterial genetic sequences are associated with instabilities that can interfere with standard industrial or laboratory practices, and might entail costly and burdensome quality control procedures.

The reduced genome strain may have a genome that is at least two percent (2%), five percent (5%), seven percent (7%) to eight percent (8%) to fourteen percent (14%) to eighteen percent (18%) to twenty percent (20%), to forty percent (40%) to sixty percent (60%) smaller than the genome of its native parental strain. The percentage by which a genome has become smaller after a series of deletions is calculated by dividing "the total number of base pairs deleted after all of the deletions" by "the total number of base pairs in the genome of the parental strain before all of the deletions" and then multiplying by 100.

The reduced genome strain may also have a genome that has about 5% to about 10%, about 10% to about 20%, about 30% to about 40%, or about 60% of its protein encoding genes deleted. The percentage by which a genome has had protein encoding genes deleted is calculated by dividing "the total number of protein encoding genes deleted after all of the deletions" by "the total number of protein encoding genes in the genome of the parental strain before all of the deletions" and then multiplying by 100.

The genes and other nucleic acid sequences deleted from the genome may not adversely affect the rate of survival and proliferation of the reduced genome strain under specific growth conditions. Whether a level of adverse effect is acceptable depends on a specific application. For example, a 30% reduction in proliferation rate may be acceptable for one application but not another. In addition, adverse effect of deleting a nucleic acid sequence from the genome may be reduced by measures such as changing culture conditions. Such measures may turn an unacceptable adverse effect to an acceptable one. The proliferation rate may be increased or approximately the same as the parental strain. The proliferation rate may also be from about 5%, 10%, 15%, 20%, 30%, 40% to about 50% lower than that of the parental strain. The doubling time of the reduced genome strain may range from about thirty minutes to about three hours.

Parent

The parental strain may be any bacteria strain or other organism, as well as an intermediate strain from which the reduced genome strain is derived. Representative examples of parent strains include, but are not limited to, *E. coli* strains such as K-12 or B, or a strain with a genome sequence substantially identical thereto. The K-12 strain may be MG1655. The nucleotide sequence of the genome of the parental strain may be partially or completely known. The complete genomic sequence of several strains of *E. coli* and other commonly used laboratory microorganisms is known (see, e.g., Blattner et al., Science, 277:1453-74, 1997; GenBank Accession No. U00096; Perna et al., Nature, 409,529-533, 2001; Hayashi et al., DNA Res., 8,11-22, 2001; Welch et al., Proc. Natl. Acad. Sci., USA 99:17020-17024, 2002 and GenBank Accession No. AE014075, each of which is incorporated herein by reference.

The nucleic acid sequence of *E. coli* MG1655 (annotated version m56) (NCBI accession no. U00096.1) has a total size of 4,639,675 nucleotides or base pairs. The original release of the genomic sequence of *E. coli* MG1655 was annotated version m54 (4,639,221 nucleotides or base pairs). Each gene that was predicted to occur in the original release of the *E. coli* MG 1655 genome was assigned a unique numeric identifier beginning with a lowercase "b". The first predicted gene was thrL with b0001; the last gene was lasT with b4403. Since the initial release, several new genes have been found which were given unauthenticated b-numbers with a suffix of "a" or "0.1" by various groups, for example yaaV. Some of these genes were accepted in the most recent annotation (version m56) and have had new b-numbers assigned starting from b4404. Several genes in the m54 version have since been shown to be merged together or split apart caused by sequencing errors. These have all been reissued new b-numbers from b4460 to b4500 and the old b-number deaccessioned.

Genomic Deletions

The reduced genome strain may be lacking one or more of the nucleic acid regions set forth on Table 1 of International Patent Application Publication No. WO 2007/024756, the contents of which are incorporated herein by reference, or sequences substantially identical thereto. Table 1 of WO 2007/024756 provides the following annotated features of the genome for *E. coli* MG1655 (annotated version m56): Column 1 (Type) lists the type of annotated feature (coding sequence (CDS), prophage, rep_origin, repeat region, rRNA, tRNA, misc_RNA or misc_feature); Column 2 (S) lists the reference strand (+: forward, −: complementary); Column 3 (Left) lists the position of the left end of the feature; Column 4 (Right) lists the position of the right end of the feature; Column 5 (Name) lists the name of the feature; and Column 6 (B) lists the Blattner number or b-number of the feature. The reduced genome strain may be MDS41, MDS42, MDS43, MDS44, MDS45, MDS46, MDS47, MDS48, MDS49, MDS50, MDS51, MDS52, MDS53, MDS54, MDS55, MDS56, MDS57, MDS58, MDS59, MDS60 or a strain with a genome substantially identical thereto. The reduced genome strain may also be MDS42recA- or a strain with a genome substantially identical thereto.

Figure 1:
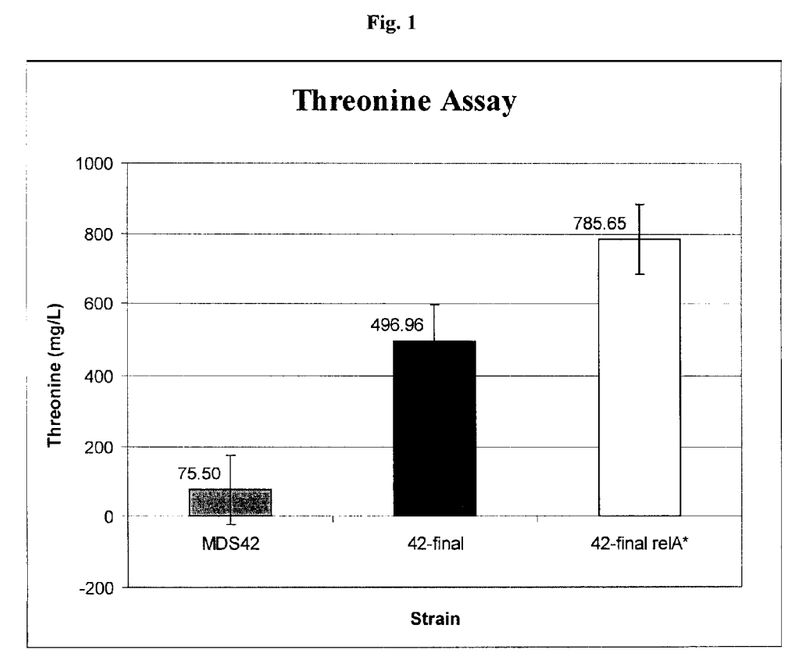
FIG. 1 shows threonine production by an MDS42 cell line, an MDS42 cell line engineered to produce threonine, and an MDS42 cell line engineered to produce threonine with a relA point mutation.

One type of nucleic acid sequence that may be deleted includes those that may adversely affect the stability of the organism or of the gene products of that organism. Such elements that give rise to instability include transposable elements, insertion sequences, and other "selfish DNA" elements that may playa role in genome instability. These elements, either intact or defective, may move from one point to another in the genome or other nucleic acid sequences in the cell, such as a vector. These elements may not be important for bacteria survival and growth in a cultured environment. Positions of the IS elements on a genome map of *E. coli* MG1655 (annotated version m54) are shown in FIG. 1 and Table 1 of U.S. Patent Publication No. 20030138937 and International Patent Publication No. WO 2003/070880, the contents of which are incorporated herein by reference. Other nucleic acid sequences associated with genomic instability may also be deleted.

Another type of nucleic acid sequence that may be deleted is the restriction modification system genes and other endogenous nucleases whose products may destroy foreign DNA. These genes may not be important for bacterial survival and growth in culture environments. These genes may also interfere with genetic engineering by destroying vectors introduced into a bacterium. Positions of restriction modification system genes on a genome map of *E. coli* MG1655 (annotated version m54) are shown in FIG. 1 and Table 1 of U.S. Patent Publication No. 20030138937 and International Patent Publication No. WO 2003/070880, the contents of which are incorporated herein by reference. DNA methylase genes, including heterologous genes, may be added back to the deleted strain so as to optimize the strain for certain uses, for example, eukaryotic methylase genes.

Another type of nucleic acid sequence that may be deleted is the flagella gene family, which may provide motility for bacteria. In cultured environments, bacteria motility may not be important for cell survival and growth and the swimming action may be metabolically very expensive, consuming over 1% of the cellular energy to no benefit. Positions of flagella genes on a genome map of *E. coli* MG 1655 (annotated version m54) are shown in FIG. 1 and Table 1 of U.S. Patent Publication No. 20030138937 and International Patent. Publication No. WO 2003/070880, the contents of which are incorporated herein by reference.

Another type of nucleic acid sequence that may be deleted is Rhs elements. Rhs elements may share a 3.7 Kb Rhs core, which may be a large homologous repeated region (there may be 5 copies in *E. coli* K-12) that may provide a means for genome rearrangement via homologous recombination. Rhs elements may be accessory elements which largely evolved in some other background and spread to *E. coli* by horizontal exchange after divergence of *E. coli* as a species. Positions of Rhs elements on a genome map of *E. coli* MG1655 (annotated version m54) are shown in FIG. 1 and Table 1 of U.S. Patent Publication No. 20030138937 and International Patent Publication No. WO 2003/070880, the contents of which are incorporated herein by reference.

Another type of nucleic acid sequence that may be deleted is the non-transcribed regions, which may be less important for cell survival and proliferation. Another type of nucleic acid sequence that can be deleted is the hsd regions, which may encode the major restriction modification gene family. Positions of non-transcribed regions and hsd regions on a genome map of *E. coli* MG1655 (annotated version m54) are shown in FIG. 1 and Table 1 of U.S. Patent Publication No. 20030138937 and International Patent Publication No. WO 2003/070880, the contents of which are incorporated herein by reference.

Other types of nucleic acid sequence that may be deleted include prophages, pseudogenes, toxin genes, pathogenicity genes, periplasmic protein genes, membrane protein genes, and bacteriophage receptors, such as [tonA] (FhuA) and/or its complete operon [fhu] ABC which encodes the receptor for the lytic phage T1.

Other types of nucleic acid sequences that may be deleted may be identified by comparing the genome of one bacterial strain to one or more others strains. Nucleic acid sequences that are not present in two or three of the strains are less likely to be functionally essential and thus may be candidates for deletion. After the sequence of *E. coli* K-12 (see Blattner, et al., supra), was compared to the sequence of its close relative 0157:H7 (See Perna et al., supra), it was discovered that 22% (K-12) and 46% (0157:H7) of the protein encoding genes may be located on strain-specific islands of from one to about 85 kb inserted randomly into a relatively constant backbone. U.S. Patent Publication No. 20030138937 and International Patent Publication No. WO 2003/070880, the contents of which are incorporated herein by reference, describe the comparison of the genomic sequences of *E. coli* strains 0157:H7 EDL933 and K-12 MG1655, which led to the identification and deletion of twelve targets resulting in a bacteria strain with a genome that is about 8% smaller. The bacteria with the reduced genome grew at substantially the same rate as the native parent MG1655 strain.

The DNA sequence of a uropathogenic *E. coli* strain CFT073 H7 (see Welch et al, supra), was recently determined and its sequence was compared to the K-12 (MG1655) and 0157:H7. Results show that only about 40% of all coding genes found in any one of the genomes are present in all of the genomes and CFT073, K-12 and 0157:H7 are composed of 67%, 43% and 68% strain specific island genes. Based on this information, as much as about 60% of the protein coding sequences may be deleted from *E. coli*. It should be noted that there may be genes essential for growth in one strain that are not required for growth in other strains. In such cases, the gene essential for growth of that strain may not be deleted from the strain or if deleted may be replaced with another gene with a complementary function so as to permit growth of the strain.

Other types of nucleic acid sequences that may be deleted are genes coding periplasmic proteins. Gram-negative bacteria, such as *E. coli*, have two cellular membranes, the inner cell membrane and the outer cell membrane, which are separated by a periplasmic space (PS). Nine known and three putative periplasmic protein genes were successfully deleted in constructing MDS40, without significantly affecting the ability of the organism to grow on minimal medium, as shown in International Patent Publication No. WO 2003/070880, the contents of which are incorporated herein by reference. These mutations affect a range of functions, including amino acid uptake, inorganic metabolism, cell membrane maintenance, sugar metabolism, and adhesion. Eliminating periplasmic proteins may reduce the contaminants in recombinant proteins expressed in the periplasm.

Approximately 85 genes have been deleted that code for known or putative membrane proteins, identified by their signal-peptide sequences. Of these 33 may be involved in flagellar structure or biosynthesis; 9 may be involved in fimbrial structure or biosynthesis; and 13 may be involved in general secretory pathways. The remainder may have a variety of known or putative functions in the cell membranes. Many of these proteins may be processed in the periplasmic space. They have also been deleted in constructing MDS40 without significantly affecting the ability of the organism to grow on minimal medium, as shown in International Patent Publication No. WO 2003/070880, the contents of which are incorporated herein by reference.

By searching for signal peptide-like sequences in annotated MG 1655 databases, and cross-relating these with the literature, 181 proteins have been identified which may be resident periplasmic proteins. A number of these proteins have been classified according to function into several groups excluding: adhesion and mobility; nutrient and salt uptake, trace element uptake; environmental sensing; defense and protection; and periplasmic protein secretion and processing. Among the genes or full operons which may be deleted are those coding for sugar and amino acid transport proteins, which may not be needed in defined minimal media say for biopharmaceutical production.

One may test the consequence of deleting one or several genes or other nucleic acid sequences from the genome. For example, after one or several genes or other nucleic acid sequences of the genome have been deleted, one can measure the survival and proliferation rate of the resultant bacteria. Although most of the above-identified genes or other nucleic acid sequences may be deleted without detrimental effect for purpose of producing a desired product, it is possible that the deletion of a specific gene or other nucleic acid sequence may have an unacceptable consequence such as cell death or unacceptable level of reduction in proliferation rate. This possibility exists because of redundancies in gene functions and interactions between biological pathways. Some deletions that are viable in a strain without additional deletions will be deleterious only in combination with other deletions. The possibility exists also because of certain methods used to identify deletion candidates. For example, one method used to identify deletion candidates is to compare two E. coli strains and select genes or other DNA sequences that are not present in both strains. While the majority of these genes and other DNA sequences are not likely to be functionally essential, some of them may be important for a unique strain. Another method used to identify deletion candidates is to identify non-transcribed regions and the possibility exists that certain non-transcribed regions may be important for genome stability.

The consequence of deleting one or several genes or other DNA sequences to be tested depends on the purpose of an application. For example, when high production efficiency is the main concern, which is true for many applications, the effect of deletions on proliferation rate and medium consumption rate can be the consequence tested. In this case, the consequence tested can also be more specific as the production speed quantity and yield per cell of a particular product. When eliminating native protein contamination is the main concern, fewer native proteins and lower native protein levels, or the absence of a specific native protein, can be the consequence tested.

Testing the consequence of deleting a gene or other DNA sequence may be important when little is known about the gene or the DNA sequence. This is another viable method to identify deletion candidates in making a bacterium with a reduced genome. This method is particularly useful when candidates identified by other methods have been deleted and additional candidates are being sought.

When the consequence of deleting a gene or other DNA sequence has an effect on the viability of the bacteria under a set of conditions, one alternative to not deleting the specific gene or other DNA sequence is to determine if there are measures that can mitigate the detrimental effects. For example, if deleting lipopolysaccharide (LPS) genes results in poor survival due to more porous cellular membranes caused by the absence from the cellular membranes of the transmembrane domain of the LPS proteins, culture conditions can be changed to accommodate the more porous cellular membranes so that the bacteria lacking the LPS genes can survive just as well as the bacteria carrying the LPS genes.

Manner of Making Deletions

The strains may be made by deleting the nucleic acid sequences using any of the several methods known to those of skill in the art for deleting genomic nucleic acid. The nucleic acid sequences may be deleted from the genome without generating any other mutations at the deletion site and without leaving any inserted nucleic acid behind (scarless deletion). If several sequential deletions are being made from a bacterial genome, it may be important not to leave any inserted nucleic acid sequences behind. Such inserted sequences, if they were left behind, may be candidate sites for undesired recombination events that would delete uncharacterized and perhaps important portions of the remaining genome from the bacteria or cause other unanticipated genome rearrangements with untoward effects.

Representative methods for making deletions in the genome of a bacteria are described in U.S. Patent Publication No. 20030138937 and International Patent Publication No. WO 2003/070880, Posfai, G. et al., J Bacteriol. 179: 4426-4428 (1997), Muyrers, J. P. P. et al., Nucl. Acids Res. 27:1555-1557 (1999), Datsenko, K. A. et al., Proc. Natl. Acad. Sci. 97:6640-6649 (2000) and Posfai, G. et al., Nucl. Acids Res. 27: 4409-4415 (1999), each of which is incorporated herein by reference. The deletion methods may be classified to those that are based on linear DNAs and those that are based on suicide plasmids. The methods disclosed in Muyrers, J. P. P. et al., Nucl. Acids Res. 27:1555-1557 (1999) and Datsenko, K. A. et al., Proc. Natl. Acad. Sci. 97:6640-6649 (2000) are linear DNA-based methods and the methods disclosed in Posfai, G. et al., J Bacteriol. 179: 4426-4428 (1997) and Posfai, G. et al., Nucl. Acids Res. 27: 4409-4415 (1999) are suicide plasmid-based methods.

Methods

The reduced genome strain may used for the production of desired products, such as recombinant proteins, nucleic acids, therapeutic products, metabolic intermediates and end products. Representative examples of recombinant proteins include, but are not limited to, insulin, interleukins, cytokines, growth hormones, growth factors, erythropoietin, colony stimulating factors, interferon, antibodies and antibody fragments. Representative examples of therapeutic products include, but are not limited to, a vaccine component, a diagnostic product, or a research reagent. Representative examples of metabolic intermediates and end products include, but are not limited to, amino acids, fatty acids, vitamins, and the like, and chemical compounds not naturally produced in the bacteria but produced as a result of metabolic pathway engineering or other genetic manipulation (see, e.g., U.S. Pat. Nos. 6,472,16 and 6,372,476, both of which are incorporated herein by reference).

Recombinant proteins may be expressed into the periplasm or cytoplasm. The expression of proteins in the periplasm is routinely used for industrial use and has been reviewed in Hanahan, [*J. Mol. Biol.*], 166:557-80, 1983; Hockney, [*Trends Biotechnol.*], 12:456-632, 1994; and Hannig et al., [*Trends Biotechnol.*], 16:54-60, 1998, each of which is incorporated herein by reference. Recombinant proteins may be produced in the periplasm by expressing fusion proteins in which they are attached to a signal peptide that causes secretion into the periplasmic space. There the signal peptide may be cleaved off by specific signal peptidases.

Constructs useful for periplasmic expression may comprise a first nucleic acid sequence encoding a signal peptide capable of mediating transport of a protein to the periplasmic space operatively linked to a second nucleic acid sequence encoding the desired protein. The signal sequence may be native to the protein being expressed. The protein transported into the periplasmic space may be biologically active. Expression of the recombinant construct may be under the control of an inducible promoter or a promoter that is constitutively expressed in the host strain. The use of inducible promoters may be advantageous when using the Sec system which may be saturable. For example, [lac]-based promoter/repressor, inducible by the non-metabolisable galactose derivative, IPTG, may be used. Such promoters may allow fine tuning of expression and secretion through the Sec system thereby optimizing periplasmic expression.

The recombinant protein may also be co-expressed with chaperones/disulfide-bond forming enzymes which may provide proper folding of the recombinant protein. Nucleic acid sequences useful for periplasmic expression of recombinant protein include, but are not limited to, those described in U.S. Pat. Nos. 5,747,662; 5,578,464; 6,335,178; and 6,022,952; Thomas et al., Mol-Micro[*Mol Micro*], (2001) 39 (1) 47-53; Weiner et al., [*Cell*], (1998) 93, 93-101; and Current Protocols in Molecular Biology [*Current Protocols in Molecular Biology*] (1994) 16.6.1-16.6.14 (Copyright 2000 by John Wiley [et al.] and Sons), each of which is incorporated herein by reference.

The reduced genome strain may also be used to clone or amplify a nucleic acid. The reduced genome strain may provide a clean, minimal genetic background that may allow the production of high quality nucleic acids. A reduced genome strain lacking selfish DNA elements, such as IS elements, may also allow the cloning of otherwise toxic genes. The reduced genome strain may also be used to produce a library, such as a genomic library.

The reduced genome strain may also be used as a vaccine by introducing heterologous genes encoding antigens capable of inducing an immune response in a host that has been inoculated with the vaccine. Reduced genome vaccines may be DNA based vaccines containing a DNA known to be capable of inducing a desired physiological response in a host (i.e., immune response).

EXAMPLES

An MDS42 derivative capable of producing large amounts of threonine was produced by engineering a number of changes into the reduced genome bacteria. These changes include deleting tdh, the gene encoding degradative threonine dehydrogenase; and introducing a plasmid containing the threonine biosynthetic genes thrABC operably regulated by a recombinant tac promoter. The thrA gene on this plasmid encodes a feedback resistant form of homoserine dehydrogenase. Threonine production by this strain is further improved by deletion of the lad gene to depress expression of the plasmid-borne thrABC genes. A final mutation, rhtA23, encoding a mutant threonine and homo serine transporter, increases secretion of threonine in the medium. The resulting strain is referred to as 42-final in FIG. 1.

Microarray analysis of transcriptional regulation of commercial threonine overproducing strains indicated the cells were perpetually locked into a starvation state, which suggests that normal regulation of the stringent response is lost in these strains. These data prompted us to look for mutations in the genes encoding proteins involved in regulating the stringent response. Two genes were initially targeted for investigation. The relA gene plays a central role in sensing the availability of charged amino acyl tRNA's and produces ppGpp, which in turn inhibits RNA polymerase, thereby initiating stringent regulation. A second gene, spoT, is involved in degrading ppGpp and thereby also indirectly regulates the stringent response by regulating intracellular levels of ppGpp. A specific mutation of relA was discovered (G→A)547 that results in a mutation of an Ala to Thr. Although appearing to be a relatively subtle change, the residue occupies a position deep within the cleft representing the major structural feature of the structural model of the protein. This cleft likely represents the active site of the enzyme.

Figure 2:
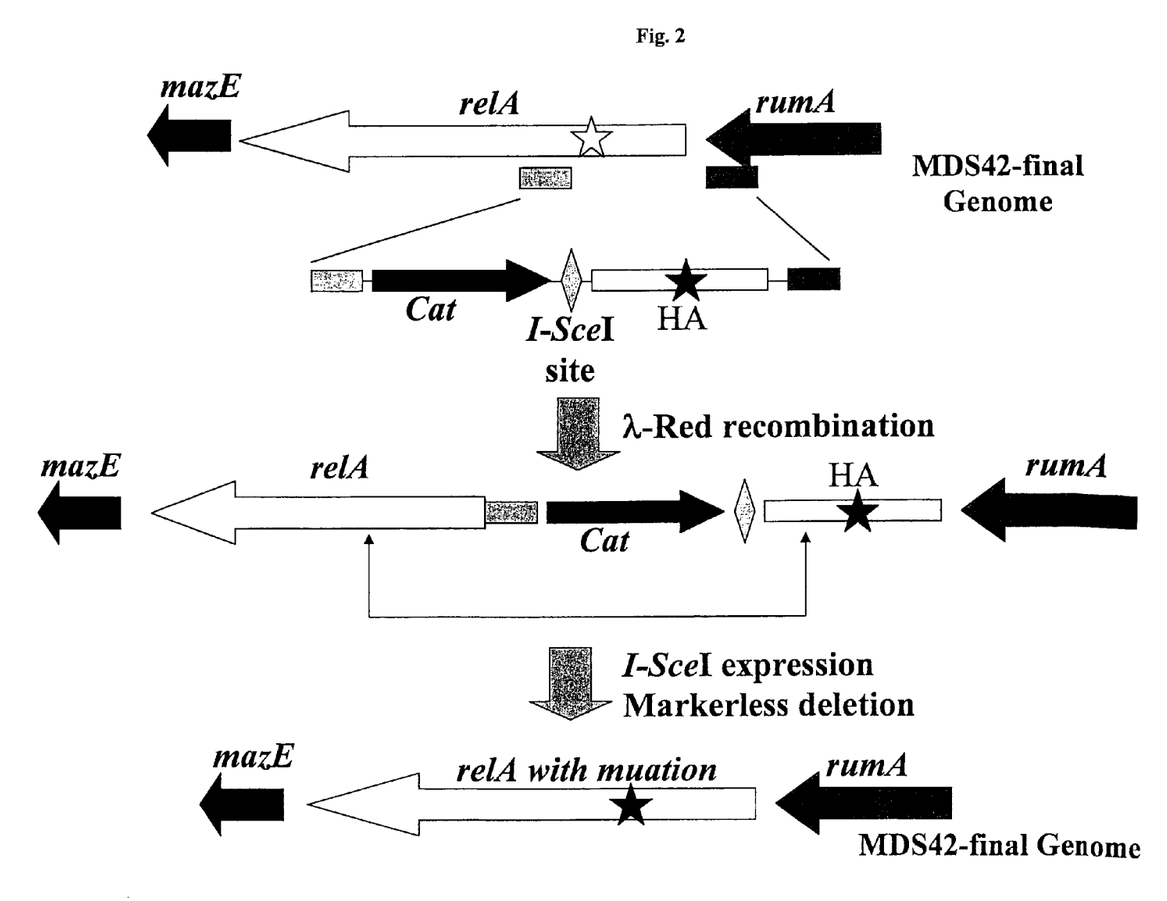
FIG. 2 shows a scheme for replacing relA of MDS42 with a mutant relA gene containing a single point mutation comprising a transversion of G to A at position 547 within the gene.

The ability of this mutation to enhance threonine production by MDSD42-final was investigated by introducing the mutation into MDS42-final. The gene was engineered by the method outlined in FIG. 2. Briefly, a PCR fragment containing a region of the mutant relA gene containing the mutated sequence was assembled such that the relA mutation was linked to a chloramphenicol acetyltransferase gene. The linear PCR fragment was electroporated into MDS42-final containing a plasmid that encodes genes for the Lambda red-gam recombinase. Recombination of the linear fragment is targeted to the relA gene on the chromosome, resulting in a chloramphenicol resistant relA merodiploid. The Lambda red-gam plasmid was cured from the chloramphenicol resistant cell and the cells were subsequently transformed with a plasmid containing an inducible I-SceI endonuclease. Inducing expression of the endonuclease results in a double stranded chromosomal break adjacent to the relA gene fragment within the chloamphenicol resistant cell. The only way the cell can survive is via recA mediated recombination of the relA gene sequences which serves to convert the relA allele present on the chromosome from the wild-type sequence to the (G→A)547 mutant sequence. Recombinants are identified by their sensitivity to chloramphenicol. The I-SceI containing plasmid is then cured from the chloramphenicol sensitive cells and the cells are transformed with the thrABC expressing plasmid.

Threonine production by MDS42, MDS42-final and MDS42-final relA* was assayed by growing the individual strains in minimal glucose media to stationary phase, removing the cells by centrifugation and filtration, and then diluting the filter sterilized spent media into fresh minimal media, and examining the combined media's ability to support growth of threonine mutant strains. The absolute levels threonine in the samples is determined by comparing the supported growth of the experimental samples and a standard curve generated with known concentrations of chemically synthesized threonine. Results shown in FIG. 1 indicate that the relA* mutation increases the ability of the MDS42-final strain significantly. This supports the hypothesis that relA* and similar relA mutants improve the ability of *E. coli* strains to produce high levels of amino acids.

What is claimed is:

1. A recombinant bacterium comprising a genome containing a relA gene wherein the relA gene contains at least one point mutation at position 547 or 548 of the coding sequence of the relA gene, wherein the mutation is selected from one or more of: the G→A mutation at position 547 set forth in SEQ ID NO:1, the G→T mutation at position 547 set forth in SEQ ID NO:2, the C→G mutation at position 548 set forth in SEQ ID NO:3, or the C→T mutation at position 548 set forth in SEQ ID NO:4.

2. The bacterium of claim 1, wherein the genome of said bacterium is genetically engineered to be at least 5% smaller than the genome of its native parent strain.

3. A method of biosynthesizing an amino acid, the method comprising: providing the bacterium of claim 1 and expressing an amino acid from the bacterium.

4. The method of claim 3 wherein the amino acid is selected from the group consisting of Ala, Arg, Asn, Asp, Cys, Gln, Glu, Gly, His, Ile, Val, Leu, Lys, Met, Phe, Pro, Ser, Thr, Tyr, and Trp.

5. A method for biosynthesizing an amino acid comprising: (1) providing the bacterium of claim 2; (2) introducing into said bacterium a plasmid containing one or more biosynthetic genes for the amino acid operably regulated by a promoter; and (3) expressing an amino acid from the bacterium.

6. The method of claim 5 wherein the one or more biosynthetic genes for the amino acid comprise thrABC operably regulated by a recombinant tac promoter.

7. The bacterium of claim 1, wherein said bacterium is an *E. coli* bacterium.

8. The bacterium of claim 2, wherein said bacterium is an *E. coli* bacterium.

* * * * *

SEQUENCE LISTING

<160> NUMBER OF SEQ ID NOS: 4

<210> SEQ ID NO 1
<211> LENGTH: 2235
<212> TYPE: DNA
<213> ORGANISM: Escherichia coli

<400> SEQUENCE: 1

| | | | | | | |
|---|---|---|---|---|---|---|
| atggttgcgg | taagaagtgc | acatatcaat | aaggctggtg | aatttgatcc | ggaaaaatgg | 60 |
| atcgcaagtc | tgggtattac | cagccagaag | tcgtgtgagt | gcttagccga | aacctgggcg | 120 |
| tattgtctgc | aacagacgca | ggggcatccg | gatgccagtc | tgttattgtg | gcgtggtgtt | 180 |
| gagatggtgg | agatcctctc | gacattaagt | atggacattg | acacgctgcg | ggcggcgctg | 240 |
| cttttccctc | tggcggatgc | caacgtagtc | agcgaagatg | tgctgcgtga | gagcgtcggt | 300 |
| aagtcggtcg | ttaaccttat | tcacggcgtg | cgtgatatgg | cggcgatccg | ccagctgaaa | 360 |
| gcgacgcaca | ctgattctgt | ttcctccgaa | caggtcgata | acgttcgccg | gatgttattg | 420 |
| gcgatggtcg | atgattttcg | ctgcgtagtc | atcaaactgg | cggagcgtat | tgctcatctg | 480 |
| cgcgaagtaa | aagatgcgcc | ggaagatgaa | cgtgtactgg | cggcaaaaga | gtgtaccaac | 540 |
| atctacacac | cgctggctaa | ccgtctcgga | tcggacaac | tgaaatggga | actgaagat | 600 |
| tactgcttcc | gttacctcca | tccaaccgaa | tacaaacgaa | ttgccaaact | gctgcatgaa | 660 |
| cggcgtctcg | accgcgaaca | ctacatcgaa | gagttcgttg | gtcatctgcg | cgctgagatg | 720 |
| aaagctgaag | gcgttaaagc | ggaagtgtat | ggtcgtccga | acacatcta | cagcatctgg | 780 |
| cgtaaaatgc | agaaaaagaa | cctcgccttt | gatgagctgt | tgatgtgcg | tgcggtacgt | 840 |
| attgtcgccg | agcgtttaca | ggattgctat | gccgcactgg | ggatagtgca | cactcactat | 900 |
| cgccacctgc | cggatgagtt | tgacgattac | gtcgctaacc | cgaaaccaaa | cggttatcag | 960 |
| tctattcata | ccgtggttct | ggggccgggt | ggaaaaaccg | ttgagatcca | aatccgcacc | 1020 |
| aaacagatgc | atgaagatgc | agagttgggt | gttgctgcgc | actggaaata | taaagagggc | 1080 |
| gcggctgctg | gcggcgcacg | ttcgggacat | gaagaccgga | ttgcctggct | gcgtaaactg | 1140 |
| attgcgtggc | aggaagagat | ggctgattcc | ggcgaaatgc | tcgacgaagt | acgtagtcag | 1200 |
| gtctttgacg | accgggtgta | cgtctttacg | ccgaaaggtg | atgtcgttga | tttgcctgcg | 1260 |
| ggatcaacgc | cgctggactt | cgcttaccac | atccacagtg | atgtcggaca | ccgctgcatc | 1320 |
| ggggcaaaaa | ttggcgggcg | cattgtgccg | ttcacctacc | agctgcagat | gggcgaccag | 1380 |
| attgaaatta | tcacccagaa | acagccgaac | cccagccgtg | actggttaaa | cccaaacctc | 1440 |
| ggttacgtca | caaccagccg | tgggcgttcg | aaaattcacg | cctggttccg | taaacaggac | 1500 |
| cgtgacaaaa | acattctggc | tgggcggcaa | atccttgacg | acgagctgga | acatctgggg | 1560 |
| atcagcctga | agaagcaga | aaacatctg | ctgccgcgtt | acaacttcaa | tgatgtcgac | 1620 |
| gagttgctgg | cggcgattgg | tggcggggat | atccgtctca | atcagatggt | gaacttcctg | 1680 |
| caatcgcaat | ttaataagcc | gagtgccgaa | gagcaggacg | ccgccgcgct | gaagcaactt | 1740 |
| cagcaaaaaa | gctacacgcc | gcaaaaccgc | agtaaagata | acggtcgcgt | ggtagtcgaa | 1800 |
| ggtgttggca | acctgatgca | ccacatcgcg | cgctgctgcc | agccgattcc | tggagatgag | 1860 |
| attgtcggct | tcattaccca | ggggcgcggt | atttcagtac | accgcgccga | ttgcgaacaa | 1920 |
| ctggcggaac | tgcgctccca | tgcgccagaa | cgcattgttg | acgcggtatg | gggtgagagc | 1980 |
| tactccgccg | gatattcgct | ggtggtccgc | gtggtagcta | atgatcgtag | tgggttgtta | 2040 |

-continued

| | |
|---|---|
| cgtgatatca cgaccattct cgccaacgag aaggtgaacg tgcttggcgt tgccagccgt | 2100 |
| agcgacacca aacagcaact ggcgaccatc gacatgacca ttgagattta caacctgcaa | 2160 |
| gtgctggggc gcgtgctggg taaactcaac caggtgccgg atgttatcga cgcgcgtcgg | 2220 |
| ttgcacggga gttag | 2235 |

<210> SEQ ID NO 2
<211> LENGTH: 2235
<212> TYPE: DNA
<213> ORGANISM: Escherichia coli

<400> SEQUENCE: 2

| | |
|---|---|
| atggttgcgg taagaagtgc acatatcaat aaggctggtg aatttgatcc ggaaaaatgg | 60 |
| atcgcaagtc tgggtattac cagccagaag tcgtgtgagt gcttagccga aacctgggcg | 120 |
| tattgtctgc aacagacgca ggggcatccg gatgccagtc tgttattgtg cgtggtgtt | 180 |
| gagatggtgg agatcctctc gacattaagt atggacattg acacgctgcg gcggcgctg | 240 |
| cttttccctc tggcggatgc caacgtagtc agcgaagatg tgctgcgtga gagcgtcggt | 300 |
| aagtcggtcg ttaaccttat tcacggcgtg cgtgatatgg cggcgatccg ccagctgaaa | 360 |
| gcgacgcaca ctgattctgt ttcctccgaa caggtcgata acgttcgccg gatgttattg | 420 |
| gcgatggtcg atgattttcg ctgcgtagtc atcaaactgg cggagcgtat tgctcatctg | 480 |
| cgcgaagtaa aagatgcgcc ggaagatgaa cgtgtactgg cggcaaaaga gtgtaccaac | 540 |
| atctactcac cgctggctaa ccgtctcgga tcggacaac tgaaatggga actggaagat | 600 |
| tactgcttcc gttacctcca tccaaccgaa tacaaacgaa ttgccaaact gctgcatgaa | 660 |
| cggcgtctcg accgcgaaca ctacatcgaa gagttcgttg gtcatctgcg cgctgagatg | 720 |
| aaagctgaag gcgttaaagc ggaagtgtat ggtcgtccga acacatcta cagcatctgg | 780 |
| cgtaaaatgc agaaaaagaa cctcgccttt gatgagctgt ttgatgtgcg tgcggtacgt | 840 |
| attgtcgccg agcgtttaca ggattgctat gccgcactgg ggatagtgca cactcactat | 900 |
| cgccacctgc cggatgagtt tgacgattac gtcgctaacc cgaaaccaaa cggttatcag | 960 |
| tctattcata ccgtggttct ggggccgggt ggaaaaaccg ttgagatcca atccgcacc | 1020 |
| aaacagatgc atgaagatgc agagttgggt gttgctgcgc actggaaata taagagggc | 1080 |
| gcggctgctg gcgcgcacg ttcgggacat gaagaccgga ttgcctggct gcgtaaactg | 1140 |
| attgcgtggc aggaagagat ggctgattcc ggcgaaatgc tcgacgaagt acgtagtcag | 1200 |
| gtctttgacg accgggtgta cgtctttacg ccgaaaggtg atgtcgttga tttgcctgcg | 1260 |
| ggatcaacgc cgctggactt cgcttaccac atccacagtg atgtcggaca ccgctgcatc | 1320 |
| ggggcaaaaa ttggcgggcg cattgtgccg ttcacctacc agctgcagat gggcgaccag | 1380 |
| attgaaatta tcacccagaa acagccgaac cccagccgtg actggttaaa cccaaacctc | 1440 |
| ggttacgtca caaccagccg tgggcgttcg aaaattcacg cctggttccg taaacaggac | 1500 |
| cgtgacaaaa acattctggc tgggcggcaa atccttgacg acgagctgga acatctgggg | 1560 |
| atcagcctga agaagcaga aaacatctg ctgccgcgtt acaacttcaa tgatgtcgac | 1620 |
| gagttgctgg cggcgattgg tggcggggat atccgtctca atcagatggt gaacttcctg | 1680 |
| caatcgcaat ttaataagcc gagtgccgaa gagcaggacg ccgccgcgct gaagcaactt | 1740 |
| cagcaaaaaa gctacacgcc gcaaaaccgc agtaaagata acggtcgcgt ggtagtcgaa | 1800 |
| ggtgttggca acctgatgca ccacatcgcg cgctgctgcc agccgattcc tggagatgag | 1860 |
| attgtcggct tcattaccca ggggcgcggt atttcagtac accgcgccga ttgcgaacaa | 1920 |

-continued

| | |
|---|---|
| ctggcggaac tgcgctccca tgcgccagaa cgcattgttg acgcggtatg gggtgagagc | 1980 |
| tactccgccg gatattcgct ggtggtccgc gtggtagcta atgatcgtag tgggttgtta | 2040 |
| cgtgatatca cgaccattct cgccaacgag aaggtgaacg tgcttggcgt tgccagccgt | 2100 |
| agcgacacca aacagcaact ggcgaccatc gacatgacca ttgagattta caacctgcaa | 2160 |
| gtgctggggc gcgtgctggg taaactcaac caggtgccgg atgttatcga cgcgcgtcgg | 2220 |
| ttgcacggga gttag | 2235 |

<210> SEQ ID NO 3
<211> LENGTH: 2235
<212> TYPE: DNA
<213> ORGANISM: Escherichia coli

<400> SEQUENCE: 3

| | |
|---|---|
| atggttgcgg taagaagtgc acatatcaat aaggctggtg aatttgatcc ggaaaaatgg | 60 |
| atcgcaagtc tgggtattac cagccagaag tcgtgtgagt gcttagccga aacctgggcg | 120 |
| tattgtctgc aacagacgca ggggcatccg gatgccagtc tgttattgtg cgtggtgtt | 180 |
| gagatggtgg agatcctctc gacattaagt atggacattg acacgctgcg ggcggcgctg | 240 |
| cttttccctc tggcggatgc caacgtagtc agcgaagatg tgctgcgtga gagcgtcggt | 300 |
| aagtcggtcg ttaaccttat tcacggcgtg cgtgatatgg cggcgatccg ccagctgaaa | 360 |
| gcgacgcaca ctgattctgt ttcctccgaa caggtcgata acgttcgccg gatgttattg | 420 |
| gcgatggtcg atgattttcg ctgcgtagtc atcaaactgg cggagcgtat tgctcatctg | 480 |
| cgcgaagtaa aagatgcgcc ggaagatgaa cgtgtactgg cggcaaaaga gtgtaccaac | 540 |
| atctacggac cgctggctaa ccgtctcgga tcggacaac tgaaatggga actggaagat | 600 |
| tactgcttcc gttacctcca tccaaccgaa tacaaacgaa ttgccaaact gctgcatgaa | 660 |
| cggcgtctcg accgcgaaca ctacatcgaa gagttcgttg gtcatctgcg cgctgagatg | 720 |
| aaagctgaag gcgttaaagc ggaagtgtat ggtcgtccga acacatcta cagcatctgg | 780 |
| cgtaaaatgc agaaaaagaa cctcgccttt gatgagctgt tgatgtgcg tgcggtacgt | 840 |
| attgtcgccg agcgtttaca ggattgctat gccgcactgg ggatagtgca cactcactat | 900 |
| cgccacctgc cggatgagtt tgacgattac gtcgctaacc cgaaaccaaa cggttatcag | 960 |
| tctattcata ccgtggttct ggggccgggt ggaaaaaccg ttgagatcca aatccgcacc | 1020 |
| aaacagatgc atgaagatgc agagttgggt gttgctgcgc actggaaata aagagggc | 1080 |
| gcggctgctg gcgcgcacg ttcgggacat gaagaccgga ttgcctggct gcgtaaactg | 1140 |
| attgcgtggc aggaagagat ggctgattcc ggcgaaatgc tcgacgaagt acgtagtcag | 1200 |
| gtctttgacg accgggtgta cgtctttacg ccgaaaggtg atgtcgttga tttgcctgcg | 1260 |
| ggatcaacgc cgctggactt cgcttaccac atccacagtg atgtcggaca ccgctgcatc | 1320 |
| ggggcaaaaa ttggcgggcg cattgtgccg ttcacctacc agctgcagat gggcgaccag | 1380 |
| attgaaatta tcacccagaa acagccgaac cccagccgtg actggttaaa cccaaaccctc | 1440 |
| ggttacgtca caaccagccg tgggcgttcg aaaattcacg cctggttccg taaacaggac | 1500 |
| cgtgacaaaa acattctggc tgggcggcaa atccttgacg acgagctgga acatctgggg | 1560 |
| atcagcctga agaagcaga aaacatctg ctgccgcgtt acaacttcaa tgatgtcgac | 1620 |
| gagttgctgg cggcgattgg tggcggggat atccgtctca atcagatggt gaacttcctg | 1680 |
| caatcgcaat ttaataagcc gagtgccgaa gagcaggacg ccgccgcgct gaagcaactt | 1740 |
| cagcaaaaaa gctacacgcc gcaaaaccgc agtaaagata cggtcgcgt ggtagtcgaa | 1800 |

```
ggtgttggca acctgatgca ccacatcgcg cgctgctgcc agccgattcc tggagatgag    1860
attgtcggct tcattaccca ggggcgcggt atttcagtac accgcgccga ttgcgaacaa    1920
ctggcggaac tgcgctccca tgcgccagaa cgcattgttg acgcggtatg gggtgagagc    1980
tactccgccg gatattcgct ggtggtccgc gtggtagcta atgatcgtag tgggttgtta    2040
cgtgatatca cgaccattct cgccaacgag aaggtgaacg tgcttggcgt tgccagccgt    2100
agcgacacca acagcaact ggcgaccatc gacatgacca ttgagattta caacctgcaa    2160
gtgctggggc gcgtgctggg taaactcaac caggtgccgg atgttatcga cgcgcgtcgg    2220
ttgcacggga gttag                                                    2235

<210> SEQ ID NO 4
<211> LENGTH: 2235
<212> TYPE: DNA
<213> ORGANISM: Escherichia coli

<400> SEQUENCE: 4
atggttgcgg taagaagtgc acatatcaat aaggctggtg aatttgatcc ggaaaaatgg      60
atcgcaagtc tgggtattac cagccagaag tcgtgtgagt gcttagccga aacctgggcg     120
tattgtctgc aacagacgca ggggcatccg gatgccagtc tgttattgtg cgtggtgtt     180 gagatggtgg agatcctctc gacattaagt atggacattg acacgctgcg ggcggcgctg     240
ctttttccct ctggcggatg caacgtagtc agcgaagatg tgctgcgtga gagcgtcggt     300
aagtcggtcg ttaaccttat tcacggcgtg cgtgatatgg cggcgatccg ccagctgaaa     360
gcgacgcaca ctgattctgt ttcctccgaa caggtcgata cgttcgccg gatgttattg     420 gcgatggtcg atgattttcg ctgcgtagtc atcaaactgg cggagcgtat tgctcatctg     480
cgcgaagtaa aagatgcgcc ggaagatgaa cgtgtactgg cggcaaaaga gtgtaccaac     540
atctacgtac cgctggctaa ccgtctcgga tcggacaac tgaaatggga actggaagat      600
tactgcttcc gttacctcca tccaaccgaa tacaaacgaa ttgccaaact gctgcatgaa     660
cggcgtctcg accgcgaaca ctacatcgaa gagttcgttg gtcatctgcg cgctgagatg     720
aaagctgaag gcgttaaagc ggaagtgtat ggtcgtccga acacatctc cagcatctgg     780 cgtaaaatgc agaaaaagaa cctcgccttt gatgagctgt tgatgtgcg tgcggtacgt     840 attgtcgccg agcgttaca ggattgctat gccgcactgg ggatagtgca cactcactat     900
cgccacctgc cggatgagtt tgacgattac gtcgctaacc cgaaaccaaa cggttatcag     960
tctattcata ccgtggttct ggggccgggt ggaaaaaccg ttgagatcca aatccgcacc    1020
aaacagatgc atgaagatgc agagttgggt gttgctgcgc actggaaata taagagggc    1080 gcggctgctg gcgcgcacg ttcgggacat gaagaccgga ttgcctggct gcgtaaactg    1140
attgcgtggc aggaagagat ggctgattcc ggcgaaatgc tcgacgaagt acgtagtcag    1200
gtctttgacg accgggtgta cgtctttacg ccgaaaggtg atgtcgttga tttgcctgcg    1260
ggatcaacgc cgctggactt cgcttaccac atccacagtg atgtcggaca ccgctgcatc    1320
ggggcaaaaa ttggcgggcg cattgtgccg ttcacctacc agctgcagat gggcgaccag    1380
attgaaatta tcacccagaa acagccgaac cccagccgtg actggttaaa cccaaacctc    1440
ggttacgtca caaccagccg tgggcgttcg aaaattcacg cctggttccg taaacaggac    1500
cgtgacaaaa acattctggc tgggcggcaa atccttgacg acgagctgga acatctgggg    1560
atcagcctga agaagcaga aaacatctg ctgccgcgtt acaacttcaa tgatgtcgac    1620
gagttgctgg cggcgattgg tggcggggat atccgtctca atcagatggt gaacttcctg    1680
```

-continued

```
caatcgcaat ttaataagcc gagtgccgaa gagcaggacg ccgccgcgct gaagcaactt    1740
cagcaaaaaa gctacacgcc gcaaaaccgc agtaaagata acggtcgcgt ggtagtcgaa    1800
ggtgttggca acctgatgca ccacatcgcg cgctgctgcc agccgattcc tggagatgag    1860
attgtcggct tcattaccca ggggcgcggt atttcagtac accgcgccga ttgcgaacaa    1920
ctggcggaac tgcgctccca tgcgccagaa cgcattgttg acgcggtatg gggtgagagc    1980
tactccgccg gatattcgct ggtggtccgc gtggtagcta atgatcgtag tgggttgtta    2040
cgtgatatca cgaccattct cgccaacgag aaggtgaacg tgcttggcgt tgccagccgt    2100
agcgacacca aacagcaact ggcgaccatc gacatgacca ttgagattta caacctgcaa    2160
gtgctggggc gcgtgctggg taaactcaac caggtgccgg atgttatcga cgcgcgtcgg    2220
ttgcacggga gttag                                                    2235
```